United States Patent [19]

Livingston et al.

[11] Patent Number: 4,710,565

[45] Date of Patent: Dec. 1, 1987

[54] THESIS OF 7-HALO-7-DEOXYLINCOMYCINS

[75] Inventors: Douglas A. Livingston, Kalamazoo; Janet E. Petre, Portage, both of Mich.

[73] Assignee: The Upjohn Company, Kalamazoo, Mich.

[21] Appl. No.: 822,044

[22] Filed: Jan. 24, 1986

Related U.S. Application Data

[63] Continuation-in-part of Ser. No. 676,157, Nov. 29, 1984, abandoned.

[51] Int. Cl.$^4$ ................................................ C07H 5/10
[52] U.S. Cl. .................................. 536/16.5; 536/16.2
[58] Field of Search ................. 536/16.2, 16.3, 16.4, 536/16.5

[56] References Cited

U.S. PATENT DOCUMENTS

| | | | |
|---|---|---|---|
| 3,435,025 | 3/1969 | Birkenmeyer ...................... | 536/16.2 |
| 3,496,163 | 2/1970 | Birkenmeyer et al. ............ | 536/16.5 |
| 3,574,186 | 4/1971 | Birkenmeyer et al. ............ | 536/16.4 |
| 3,580,904 | 5/1971 | Morozowich et al. ............ | 536/16.3 |

*Primary Examiner*—J. R. Brown
*Assistant Examiner*—Elli Peselev
*Attorney, Agent, or Firm*—Sidney B. Williams, Jr.

[57] ABSTRACT

Process for preparing clindamycin and analogs thereof by reacting lincomycin or an analog thereof with a dimethylformamide and an excess of thionyl halide.

15 Claims, No Drawings

THESIS OF 7-HALO-7-DEOXYLINCOMYCINS

CROSS-REFERENCE TO RELATED APPLICATIONS

The present application is a continuation-in-part application of Ser. No. 676,157 filed Nov. 29, 1984, now abandoned.

BACKGROUND OF THE INVENTION

1. Field of the Invention

The present invention is an improved process for preparing 7-halo-7-deoxylincomycins, including clindamycin, and pharmaceutically acceptable forms thereof from lincomycin and analogs thereof. Clindamycin is a well known antibiotic that has pharmacologically useful properties.

2. Prior Art

Processes for preparing 7-halo-7-deoxylincomycins are known. U.S. Pat. Nos. 3,435,025, 3,496,163 and 3,509,127 disclose a process in which the 7-hydroxyl group of lincomycin and analogous compounds are replaced with a halogen group by reacting said compounds with a Rydon reagent and heating the resulting product. The use of thionyl chloride to convert lincomycin and analogous compounds to 7-chloro-7-deoxy compounds is described in U.S. Pat. Nos. 3,496,163, 3,509,127 and 3,574,186. The temperature needed to effect the transition described in these patents in neutral solvents, are well above room temperature. In this regard, all of the examples disclose the reaction being conducted by refluxing in carbon tetrachloride (about 77° C.).

A process for preparing 7-halo-7-deoxylincomycin by the use of a sulfite-protected lincomycin and Rydon reagents is described in U.S. Pat. No. 3,714,141.

The use of a Vilsmeier reagent to substitute a halo atom for a hydroxyl group has been described. Eilingsfield et al, Angew. Chem. 72, 836 (1960) and Eilengsfield et al, Chem. Ber. 96 2671 (1963). Evans et al, JOC 33, 1074 (1968) discloses on page 1075 that while a Vilsmeier reagent prepared from methanesulfonyl chloride and dimethylformamide was successfully used to replace a primary hydroxyl group, it was not in attempts to replace a secondary hydroxyl group.

The structure of the adduct formed between dimethylformamide and thionyl chloride from which sulfur dioxide has not been removed has been investigated by Ferre et al, Tet. Lett. 2161 (1969) and the conditions for converting the dimethylformamide thionyl chloride adduct to the corresponding amide chloride has been described; Kikagawa et al, Chem. Pharm, Bull. 19, 2629 (1971). Bosshard et al, Helv. Chim. Acta. 42, 16153 (1959) discloses the use of dimethyl formamide as a catalyst in the conversion of carboxylic acids to acid chlorides.

Hepburn et al, J. Chem. Soc. Perkin I, 754 (1976) and Hepburn et al, Chem. & Ind. 664 (1974) describes the use of amide chlorides obtained from Vilsmeier reagents to replace hydroxyl groups by chlorine or bromine groups. However, the hydroxyl containing compounds were relatively simple alcohols and did not approach the complexity of the lincomycin molecule.

The use of a mixture of mesyl chloride and N,N-dimethylformamide to replace primary groups of hexopyranosides by chlorine is described by Edwards et al, Tetrahedron Letters, 2369 (1973).

The halogenation of nucleosides by amide chlorides is described by Dobs et al, Tetrahedron Letters, 165 (1969).

While the prior art describes the use of both Vilsmeier reagents and amide chlorides obtained therefrom in reactions similar to that of the process of this instant invention, the prior art is confusing at best. This is particularly true with respect to whether or not it is preferred to use the Vilsmeier reagent or to remove sulfur dioxide from it and use the resulting amide chloride.

Applicant's copending application Ser. No. 610,364, filed May 15, 1984, now U.S. Pat. No. 3,568,741 discloses a process wherein amide chlorides are used to convert lincomycin-type compounds to 7-halo-7-deoxylincomycin-type compounds. Reaction temperatures of about 50°–75° C. and reaction times of 4 to 10 hours are generally required.

To applicant's knowledge, however, none of the prior art processes can be conducted under the mild conditions used in the process claimed herein.

SUMMARY OF INVENTION 7-halo-7-deoxy lincomycin and analogs thereof are prepared by reacting lincomycin, with thionyl halide and dimethylformamide. The reaction can be conducted by (1) allowing the product of reaction between lincomycin or one of its analogs and an excess of thionyl halide to react in a solvent that is substantially composed of dimethylformamide or (2) by treating a mixture of lincomycin or one of its analogs and dimethylformamide with an excess of thionyl halide. In alternative (1) the solvent may contain some of the solvent used in the reaction between the lincomycin and thionyl chloride (i.e., methylene chloride).

The unusually mild conditions of the reaction coupled with the ease in which it can be performed and low energy requirements are some of the advantages of the process of this invention. For instance, the use of special equipment required for processes conducted under more extreme conditions is not required.

It has been found that the order of addition of the reactants is critical to achieving this result. We have found that a useful rate of reaction is achieved at less than 40° C. only if these orders of addition described herein are used. Otherwise, conditions appear normal for the amide chloride or thionyl chloride in inert solvent methods.

DETAILED DESCRIPTION OF THE INVENTION

Utilizing either route (1) or (2) of the invention the reaction is conducted at a temperature of about 0° C. to 50° C. for a period of about 10 to about 48 hours. The preferred temperature is about 15° C. to 30° C. and the preferred reaction time is about 1 to 5 hours.

It is preferred to conduct the reaction with an excess of thionyl chloride. As used herein the term "excess thionyl halide" means about four to thirteen equivalents of halide per equivalent of lincomycin or analog thereof. The preferred ratio of thionyl halide to lincomycin or analog thereof is about four to six equivalents.

Starting materials for the process are lincomycin or one of its analogs and a thionyl halide and dimethylformamide.

Lincomycin is a known antibiotic and methods for preparing it and its analogs are well known in the art and illustrated in U.S. Pat. Nos. 3,086,912 and 3,155,580. In addition to those described in the patents cited above, analogs of lincomycin are also exemplified in U.S. Pat. No. 3,380,992, and by protected lincomycin and analogs such as methylthiolincosaminide, 3,4-cumylidene-lincomycin, and 3,4-benzylidene-lincomycin. As used herein lincomycin, lincomycin analogs, 7-halo-7-deoxylincomycin and analogs thereof, means the free base or their salts. The salts may be anhydrous or hydrated.

The following described examples of the process for preparing 7-halo-7-deoxylincomycin and intermediates useful therein are indicative of the scope of this invention and are not to be construed as limitative.

EXAMPLE 1

Into an oven-dried round bottom flask containing a magnetic stirring bar under a nitrogen atmosphere is added methylene chloride (53 ml., 1.5 volume of thionyl chloride) and thionyl chloride (35 ml., 479 mmole). The resulting solution is cooled in an ice bath, and lincomycin hydrochloride monohydrate (35.0 g., 75.1 mmole, 3.90% $H_2O$) by Karl Fischer titration) is added via a solid addition apparatus, slowly over 30 minutes. The residual solid is rinsed in with 4 ml. methylene chloride. The resulting mixture is stirred at 0° for 15 minutes to effect complete dissolution. With ice-acetone cooling, N,N-dimethylformamide (70 ml., 900 mmole) is slowly added, keeping the temperature below 5° C. (required $\approx$30 minutes). The cooling bath is removed and house vacuum is applied to the yellow solution. A dry ice/acetone trap is used. Over a 2¼ hour period the reaction temperature increased to room temperature at which time a mild exotherm to 29° is noticed with more gas evolution. The temperature is adjusted to 25° with a water bath and the gas evolution ceased. At this point, thin layer chromatography indicates a very clean reaction to clindamycin with very little lincomycin remaining. The water bath is removed and the reaction is allowed to stir under vacuum for another hour (total reaction time of 3¼ hours). The resulting red colored solution is cooled to near 0° and anhydrous methanol (40 ml.) is added slowly. Via cannula, the reaction is quenched into 114 g. of 50% sodium hydroxide in 200 g. ice cooled to near $-10°$ C., keeping the temperature below 37°. Near the end of the quench additional 50% sodium hydroxide is used to keep the pH above 11. The resulting mixture is stirred at 37°–4° C. for 45 minutes.

The mixture is cooled to room temperature and pH is adjusted to 7 with concentrated hydrochloric acid. The solution is concentrated in vacuo to approximately one-half the volume to remove all the methanol. With ice bath cooling, the solution is adjusted to pH 1.5 with concentrated hydrochloric acid, at which time the mixture becomes homogenous. Methylene chloride (100 ml.) is added and the phases are separated. The organic phase is successively extracted through (3×150 ml.) pH 1.5 aqueous phases (0.5 M potassium hydrogen phosphate buffer adjusted to pH 1.5 with concentrated hydrochloric acid). Any interface is retained with the aqueous phase. Each aqueous phase is reextracted with (4×150 ml) methylene chloride. All four aqueous phases are combined and adjusted to pH 10.2 with 50% sodium hydroxide and then to pH 8.2 with concentrated hydrochloric acid (ice is added to keep temperature $-25°$ C.). Methylene chloride (100 ml.) is added and the phases are separated. The organic phase is extracted through (2×100 ml) pH 6.2 (0.5 M) phosphate buffer. The pH 8.2 and pH 6.2 aqueous phases are sequentially reextracted with (4×5 ml) methylene chloride. The combined organics are dried over sodium sulfate and evaporated to an oil. Residual methylene chloride is removed by two ethyl acetate azeotropes. The oil is dissolved in ethyl acetate (158 ml.) and absolute ethanol (47 ml.). Clindamycin hydrochloride ethanol solvate is obtained by seeding the solution with clindamycin hydrochloride ethanol solvate while simultaneously adjusting the pH to 1.0–1.5 with concentrated hydrochloric acid. After stirring at room temperature for one hour, then 0° for 45 minutes, the slurry is filtered and rinsed with ethyl acetate. After drying for 3 hours under vacuum, the product weighs 17.04 g., which corresponds to 68.1% yield of climdamycin hydrochloride ethanol solvate.

EXAMPLE 2

Into an oven-dried round bottom flask containing a magnetic stirring bar under a nitrogen atmosphere is added lincomycin hydrochloride (35.0 g., 79 mmole, 0.974% water by Karl Fischer titration) and N,N-dimethylformamide (125 ml.). The slurry is cooled to near 0° C. and thionyl chloride (35 ml., 474 mmole) is added over one hour. After two hours at room temperature the reaction is complete. Following cooling to near 0° C., anhydrous methanol (75 ml.) is added slowly. The solution is stirred for one hour at room temperature. Via cannula, the reaction is quenched into 114 g. of 50% sodium hydroxide in 200 g. ice and 200 ml. methylene chloride, precooled to near $-10°$, keeping the temperature below 16° C. Near the end of the quench, additional 50% sodium hydroxide is used to maintain a pH of 10.5.

Additional (100 ml.) methylene chloride is added while stirring at room temperature for three hours at pH 10.5. The pH is adjusted to 7 and the reaction is left at room temperature overnight. The mixture is concentrated in vacuo to approximately one-half the volume. Methylene chloride (100 ml.) is added, and with ice bath cooling, the pH is adjusted to 1.5 with concentrated hydrochloric acid. The layers are separated and the organic phase is successively extracted through (3×150 ml.) pH 1.5 aqueous phases (0.5 M potassium hydrogen phosphate adjusted to pH 1.5 with concentrated hydrochloric acid). Any interface layer is retained with the aqueous phase. Each aqueous phase is reextracted with (4×50 ml) methylene chloride.

The last two aqueous phases are extracted with additional (2×100 ml.) methylene chloride. All four aqueous phases are combined and the pH adjusted to 10.5 with 50% sodium hydroxide. Ice is used to maintain the solution at room temperature. Methylene chloride (100 ml.) is added and the phases are separated. The organic phase is extracted through (2×130 ml.) pH 6.2 phosphate buffer (0.5 M). The pH 10.5 and two pH 6.2 aqueous phases are reextracted with (4×50 ml.) methylene chloride. The organics are dried over sodium sulfate and concentrated in vacuo to an oil. Residual methylene chloride is removed by two ethyl acetate azeotropes. The oil is dissolved in ethyl acetate (157 ml.) and absolute ethanol solvate (45 ml.). Clindamycin hydrochloride ethanol solvate is obtained by seeding the solution with clindamycin hydrochloride ethanol while simultaneously adjusting the pH to 1.0–1.5 with concentrated hydrochloric acid. After stirring at room temperature for one hour, then 0° C. for 45 minutes, the slurry is filtered and rinsed with ethanol acetate. After drying the filter cake under vacuum for one hour, 26.65 g (66.5% yield) of clindamycin hydrochloride ethanol solvate is recovered. Clindamycin hydrochloride hydrate is recovered from the ethanol solvate by conventional means.

EXAMPLE 3

Into an oven dried round bottom flask containing a magnetic stirring bar under nitrogen atmosphere is added methylene chloride (12.5 ml., 1.5 volume of thionyl chloride) and thionyl chloride (8.25 ml., 113 mmole). The solution is cooled in an ice bath and lincomycin hydrochloride (10 g., 22.6 mmole, by Karl Fischer titration 0.974 weight % water) is added via solid addition apparatus slowly over 25 minutes. The resulting pale-pink mixture is allowed to stir at 0° until it becomes homogeneous (15 minutes). LiCl (4.8 g., 113 mmole, dried 7 hours at 130° C. and 2 mm Hg) is added. With ice-acetone cooling, N,N-dimethylformamide (17.6 ml., 226 mmole) is slowly added, keeping the temperature below 5° C. The cooling bath is removed and house vacuum is applied. Within 20 minutes the reaction mixture becomes a gel. Dimethylformamide (10 ml.) is added to facilitate stirring. After 4¼ hours, the reaction is complete by thin layer chromatography; methylene chloride (40 ml.) is added, and the reaction is cooled to near 0° C. Via cannula, the reaction is quenched into 27.2 g. of 50% sodium hydroxide and 100 g. ice cooled to near −10° C., keeping the temperature below +20° C. Towards the end of the quench additional 50% sodium hydroxide is used to keep the pH greater than 11. After stirring for two hours at pH 10-11 and room temperature, the pH is adjusted to 7 with concentrated hydrochloric acid and the mixture is left at room temperature overnight. The pH is readjusted to 10 with 50% sodium hydroxide and the layers are separated. The organic phase is extracted through (4×75 ml.) pH 1.5 aqueous phases consecutively (0.5 M potassium hydrogen phosphate adjusted to pH 1.5 with concentrated hydrochloric acid). The pH 10 aqueous phase is reextracted with (4×50 ml.) methylene chloride, carrying each wash through the four pH 1.5 phases successively. The aqueous phases are combined and adjusted to pH 10.5 with 50% sodium hydroxide. Methylene chloride (100 ml.) is added and the layers are separated. The organic phase is successively extracted through (2×75 ml) pH 6.2>0.1 (0.5 molar) phosphate buffer. The pH 10.5 and the two pH 6.2 aqueous phases are reextracted with (4×50 ml.) methylene chloride. The organics are dried over sodium sulfate and evaporated to an oil. Residual methylene chloride is removed by two ethyl acetate azeotropes. The remaining oil is dissolved in ethyl acetate (25 ml.) and stirred at room temperature for 45 minutes with activated carbon (0.5 g DARCO grade G-60). After filtering through celite 545, the filtrate is evaporated to dryness. The resulting oil is dissolved in ethyl acetate (45 ml.) and absolute ethanol (12.9 ml.). Clindamycin hydrochloride ethanol solvate is obtained by seeding this solution with clindamycin hydrochloride ethanol solvate while simultaneously adjusting the pH to 1.0–1.5 with concentrated hydrochloric acid. After stirring at room temperature for one hour, then 0° for 30 minutes, the slurry is filtered and rinsed with room temperature ethyl acetate. After drying for 1½ hour under vacuum the product weighs 8.25 g., which corresponds to 72% yield of clindamycin hydrochloride ethanol solvate.

We claim:

1. A process for preparing a compound selected from the group consisting of 7-halo-7-deoxylincomycin and analogs thereof which comprises reacting a compound selected from the group consisting of lincomycin and analogs thereof with thionyl halide and dimethylformamide under mild conditions.

2. A process according to claim 1 wherein the product of reaction between a compound selected from the group consisting of lincomycin and analogs thereof and thionyl halide is reacted with dimethylformamide.

3. A process according to claim 2 wherein the product of reaction of lincomycin and an excess of thionyl chloride is reacted with dimethylformamide to prepare clindamycin.

4. A process according to claim 3 wherein lincomycin hydrochloride is reacted with from four to thirteen equivalents of thionyl chloride, at less than 50° C., and the product therefrom is then allowed to react in a solvent selected from the group consisting of (a) dimethylformamide and (b) dimethylformamide that contains some of the solvent used in the reaction between lincomycin hydrochloride and thionyl chloride, at a temperature of about 0° C. to below 50° C. to prepare clindamycin.

5. A process according to claim 1 wherein a mixture of a compound selected from the group consisting of lincomycin and analogs thereof and dimethylformamide is reacted with an excess of thionyl halide.

6. A process according to claim 3 wherein a mixture of lincomycin and dimethylformamide is reacted with an excess of thionyl chloride to prepare clindamycin.

7. A process according to claim 6, wherein a mixture of lincomycin hydrochloride and dimethylformamide is treated with from four to thirteen equivalents of thionyl chloride and allowed to react at 0° C. to 50° C. to prepare clindamycin.

8. A process according to claim 5 wherein the compound is lincomycin.

9. A process according to claim 3 wherein the reaction is conducted at a temperature below 40° C.

10. A process according to claim 9 wherein the reaction is conducted at a temperature between 15° and 30° C.

11. A process according to claim 8 wherein the reaction is conducted at a temperature below 40° C.

12. A process according to claim 11 wherein the reaction is conducted at a temperature between 14° C. and 30° C.

13. A process according to claim 1 wherein the product prepared is converted to one of its salts.

14. A process according to claim 4 wherein clindamycin is converted to its hydrochloride.

15. A process according to claim 8 wherein the product prepared is converted to its hydrochloride.

* * * * *

UNITED STATES PATENT OFFICE
CERTIFICATE OF CORRECTION

Patent No. 4,710,565     Dated  December 1, 1987

Inventor(s)  Douglas A. Livingston

It is certified that error appears in the above-identified patent and that said Letters Patent are hereby corrected as shown below:

Title now reads: "Thesis of 7-halo-7-deoxylincomycins" and should read -- Synthesis of 7-halo-7-deoxylincomycins --.

Signed and Sealed this

Twenty-sixth Day of July, 1988

Attest:

DONALD J. QUIGG

Attesting Officer     Commissioner of Patents and Trademarks